(12) United States Patent
Geldart et al.

(10) Patent No.: US 12,203,520 B2
(45) Date of Patent: Jan. 21, 2025

(54) COMPOSITE SPRINGS, COMPOSITE SPRING ASSEMBLIES, AND METHODS FOR MAKING THE SAME

(71) Applicant: GRD Innovations LLC, Daytona Beach, FL (US)

(72) Inventors: Michael Geldart, Daytona Beach, FL (US); Tyler James Farnese, Port Orange, FL (US); Yeram Lim, Port Orange, FL (US)

(73) Assignee: GRD Innovations LLC, Daytona Beach, FL (US)

( * ) Notice: Subject to any disclaimer, the term of this patent is extended or adjusted under 35 U.S.C. 154(b) by 431 days.

(21) Appl. No.: 17/678,914

(22) Filed: Feb. 23, 2022

(65) Prior Publication Data
US 2022/0186804 A1  Jun. 16, 2022

Related U.S. Application Data

(63) Continuation of application No. PCT/US2019/048897, filed on Aug. 29, 2019.

(51) Int. Cl.
*F16F 1/20* (2006.01)
*A61F 5/01* (2006.01)

(52) U.S. Cl.
CPC .............. *F16F 1/20* (2013.01); *A61F 5/0123* (2013.01); *A61F 2005/0169* (2013.01);
(Continued)

(58) Field of Classification Search
CPC .. A61F 5/0123; A61F 2/66; A61F 2/76; A61F 2/6607; A61F 2005/0169; A61F 2005/0179; A61F 2002/30469; A61F 2002/30507; A61F 2002/5003; A61F 2002/5055; A61F 2002/6614;
(Continued)

(56) References Cited

U.S. PATENT DOCUMENTS

| 4,411,159 | A | * | 10/1983 | Spear ................... | G01L 1/2206 248/560 |
| 5,244,189 | A | * | 9/1993 | Pierman ................ | F16F 1/20 267/51 |

(Continued)

OTHER PUBLICATIONS

Walck, Christine; "Biomechanical Response of the Knee Complex to a Non-Linear Spring-Loaded Knee Joint Orthosis," Dissertations and Theses, 458 (2019).

*Primary Examiner* — Robert A. Siconolfi
*Assistant Examiner* — San M Aung
(74) *Attorney, Agent, or Firm* — Greenberg Traurig, LLP

(57) ABSTRACT

Composite springs, composite spring assemblies, medical devices including the same, and methods of making and using the same are disclosed. The composite springs may comprise alternating layers of carbon fiber and fiberglass materials. A strengthening adhesive, such as an epoxy, may be used to bind the carbon fiber and fiberglass materials. A dampening member may be attached to the composite spring, thereby at least partially defining a composite spring assembly. The dampening member may dampen elastic/spring forces of the composite spring. The composite spring assembly may be attached to an orthotic device to provide a non-linear spring response during movement of the device.

20 Claims, 10 Drawing Sheets

(52) U.S. Cl.
CPC ... *A61F 2005/0179* (2013.01); *F16F 2224/02* (2013.01); *F16F 2226/042* (2013.01); *F16F 2238/022* (2013.01)

(58) Field of Classification Search
CPC ...... A61F 2220/0025; A61F 2220/0041; F61F 1/20; F16F 2224/02; F16F 2226/042; F16F 2238/022; A61L 27/44; A63B 5/08; A63B 5/10; A63B 2209/023
USPC .......................................................... 267/158
See application file for complete search history.

(56) References Cited

U.S. PATENT DOCUMENTS

| | | | | |
|---|---|---|---|---|
| 5,464,442 | A * | 11/1995 | Burt | A61F 2/601 |
| | | | | 267/140.13 |
| 5,783,278 | A * | 7/1998 | Nishimura | D03D 49/22 |
| | | | | 428/102 |
| 6,514,293 | B1 * | 2/2003 | Jang | A61F 2/66 |
| | | | | 623/55 |
| 2012/0034833 | A1 * | 2/2012 | Schaube | B29C 70/086 |
| | | | | 428/447 |
| 2012/0211931 | A1 * | 8/2012 | Fane De Salis | F16F 1/368 |
| | | | | 267/158 |
| 2013/0001845 | A1 * | 1/2013 | Voigt | F16F 1/368 |
| | | | | 267/158 |
| 2017/0307042 | A1 * | 10/2017 | Zander | B32B 5/024 |

* cited by examiner

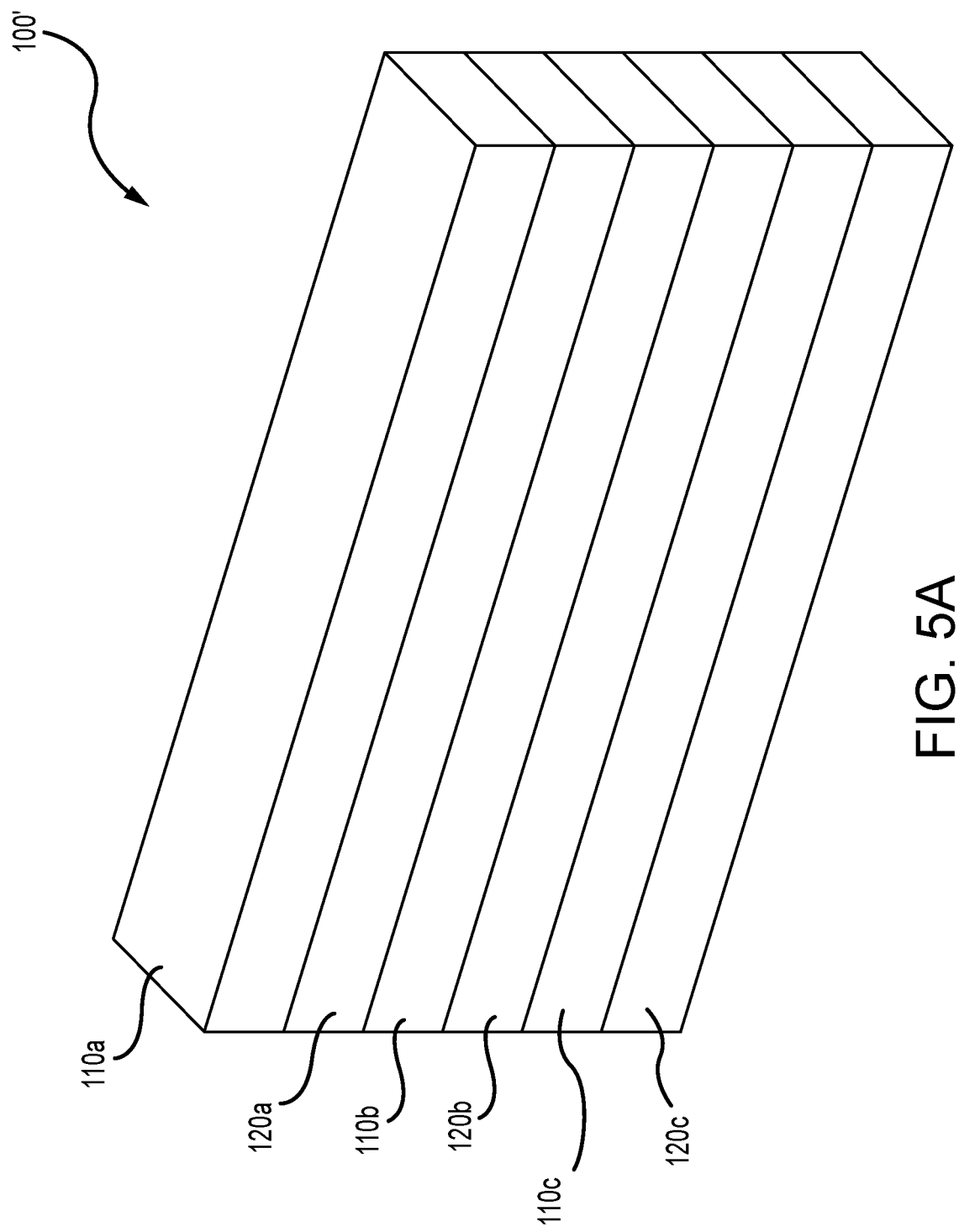

COMPOSITE SPRINGS, COMPOSITE SPRING ASSEMBLIES, AND METHODS FOR MAKING THE SAME

CROSS-REFERENCE TO RELATED APPLICATION

This application is a continuation of International Patent Application No. PCT/US2019/048897, filed Aug. 29, 2019, entitled "COMPOSITE SPRINGS, COMPOSITE SPRING ASSEMBLIES, AND METHODS FOR MAKING THE SAME", which is incorporated herein by reference in its entirety.

BACKGROUND

An estimated 6,664,324 knee injuries presented to U.S. emergency departments from 1999 through 2008, for a rate of 2.29 knee injuries per 1,000 population. (Source: https://www.ncbi.nlm.nih.gov/pubmed/22506941.) Successfully rehabilitating from a knee injury can involve considerable time and effort. Commonly-owned U.S. Patent Application Publication No. 2019/0209358 describes a variable radius spring assembly for use in orthopedic devices, such as a knee brace. The device provides a full range knee orthotic that provides support to the leg muscles without compromising the range of motion and the patient's normal walk/gate. Furthermore, the device provides lateral protection and support to the knee joint. The device is ergonomic and robust enough to be worn during activities of daily life and most athletic endeavors.

SUMMARY OF THE INVENTION

Broadly, the present patent application relates to composite springs, composite spring assemblies, and the like for use in medical devices, such as orthotic devices and prosthetic devices. A composite spring generally comprises alternating layers of a carbon fiber material and a fiberglass material. A strength adhesive (e.g. epoxy) is generally used to bind the carbon fiber materials and the fiberglass materials. The composite spring generally provides an appropriate elastic response for the composite spring assembly. In one embodiment, an appropriate number of carbon fiber layers and fiberglass layers are selected to provide a preselected non-linear spring response. The appropriate number of layers may be selected, for instance, based on one or more of patient attributes, type of medical device, and expected device lifetime, among others. In one embodiment, a composite spring facilitates realization of a non-linear spring response in a medical device.

A composite spring may be attached to a dampening member. The dampening member may facilitate dampening of the elastic response during spring-back of the composite spring. In one embodiment, the dampening member comprises a dampening plastic. In one embodiment, the dampening member comprises a nylon-based plastic. A dampening adhesive may be used to bind the composite spring to the dampening member. The dampening adhesive may facilitate dampening of the elastic response during spring-back of the composite spring. In one embodiment, the dampening adhesive realizes a lower adhesive strength than the strength adhesive of the composite spring. In one embodiment, the dampening adhesive may comprise a cyanoacrylate adhesive. In other embodiments, a strength adhesive is used in lieu of the dampening adhesive.

In one embodiment, a composite spring assembly comprises a first layer, wherein the first layer comprises a carbon fiber material, a second layer, wherein the second layer comprises a fiberglass material, a first adhesive binding the first layer and the second layer, a third layer, wherein the third layer comprises a dampening plastic, and a second adhesive joining the third layer to one of the first layer or the second layer. In one embodiment, the first adhesive is a strength adhesive. In one embodiment, the strength adhesive comprises an epoxy. In one embodiment, the second adhesive is different than the first adhesive. In one embodiment, the second adhesive is a dampening adhesive. In one embodiment, the dampening adhesive comprises a cyanoacrylate adhesive. In one embodiment, the second adhesive has a lower adhesion strength than the first adhesive. In another embodiment, the second adhesive is the same as the first adhesive. In one embodiment, the carbon fiber material comprises a carbon fiber fabric. In one embodiment, the fiberglass material comprises a fiberglass fabric. In another embodiment, the dampening plastic is a nylon-based plastic. In one embodiment, the first layer and the second layer are rectangular. In one embodiment, the first layer and the second layer are the same size. In one embodiment, the third layer is rectangular. In one embodiment, the third layer is longer than the first layer and the second layer. In one embodiment, the third layer has the same width as the first layer and the second layer.

The combination of the composite spring and the dampening member may at least partially define a composite spring assembly. In one embodiment, the composite spring assembly is a multi-composite spring assembly having at least two composite springs. In one embodiment, the number of composite springs utilized in the multi-composite spring assembly is selected based on one or more of patient attributes, type of medical device, and expected device lifetime, among others. In one embodiment, a first composite spring (a first component) is joined to a second composite spring (a second component) via an appropriate joining adhesive. In one embodiment, the joining adhesive is a dampening adhesive. In one embodiment, each of the first and second composite springs comprises alternating layers of carbon fiber and fiberglass materials. In one embodiment, a strength adhesive is used to bind the layers of the first composite spring and/or the second composite spring. In one embodiment, for both the first composite spring and the second composite spring, a strength adhesive adheres a carbon fiber material to a fiberglass material. In one embodiment, the second composite spring is attached to the dampening member via an appropriate adhesive (e.g., a dampening adhesive). In one embodiment, the first composite spring comprises at least three layers of the carbon fiber material and at least three layers of fiberglass material. In one embodiment, the second composite spring comprises the same amount of carbon fiber materials layers and fiberglass fabric layers as the first component. In one embodiment, a first adhesive adheres a carbon fiber layer of the first composite spring to a fiberglass layer of the second composite spring. In one embodiment, a second adhesive adheres a carbon fiber layer of the second composite spring to the dampening member. In one embodiment, at least one of the first adhesive and the second adhesive comprises a dampening adhesive.

The composite spring assembly may comprises additional components. In one embodiment, the composite spring assembly comprises a head. The head may be used for, inter alia, attaching the composite spring assembly to the medical device. In one embodiment, the head is attached to at least the dampening member. In one embodiment, the head is integral with the dampening plastic. For instance, a base member may comprise the head and the dampening member as integral members.

In one embodiment, the head comprises one or more slots and/or apertures to facilitate connection of the composite spring assembly to the medical device. Thus, the head may be adapted to attach to a medical device. For instance, a fastener, such as a screw, may be used to attach the head to the medical device. In one embodiment, the medical device is an orthotic device, such as a brace for a knee, elbow, ankle, wrist, or foot In another embodiment, the medical device is a prosthetic device, such as a prosthesis for an arm or leg. In one embodiment, during movement of the medical device, the composite spring provides a non-linear spring response.

In one embodiment, the head comprises a slot. In one embodiment, portions of the composite spring are located in the slot. In one embodiment, the composite spring is a multi-component composite spring and portions of the first component and the second component are located in the slot. In one embodiment, not greater than 50% of the volume of composite spring is located in the slot. In one embodiment, the head comprises a fulcrum, wherein, when the composite spring is sufficiently deflected, the fulcrum is configured to engage an upper portion of the composite spring (e.g., a fiberglass layer of the composite spring).

As noted previously, patient attributes may be used to rapidly fabricate composite springs having appropriate properties. In one embodiment, a method includes (a) determining at least one patient attribute for an orthotic patient, (b) correlating the at least one patient attribute to at least one composite spring requirement for the orthotic patient, (c) based on the determining step, selecting a composite spring for use in an orthotic device for the orthotic patient, and (d) attaching the selected composite spring to the orthotic device. These methods may be also used relative to prosthetic devices. In one embodiment, the selecting step (c) comprises selecting a number of alternating layers of carbon fiber and fiberglass for the composite spring. In one embodiment, the alternating layers comprise at least three carbon fiber layers and at least three fiberglass layers.

In one embodiment, a method includes, based on the determining step (a), selecting a multi-component composite spring for use in an orthotic or prosthetic device, wherein the alternating layers define a first component of the composite spring assembly, wherein the composite spring assembly comprises a second component attached to the first component, wherein the second component comprises alternating layers of carbon fiber and fiberglass. In one embodiment, a dampening adhesive joins the first component to the second component. In one embodiment, for both the first component and the second component, a strength adhesive binds the alternating layers of the carbon fiber and the fiberglass.

These and other aspects, advantages, and novel features of this new technology are set forth in part in the description that follows and will become apparent to those skilled in the art upon examination of the following description and figures, or may be learned by practicing one or more embodiments of the technology provided for by the present disclosure.

BRIEF DESCRIPTION OF THE DRAWINGS

FIG. 5A is a close-up, perspective view of one embodiment of a six-layered composite spring (100').

DETAILED DESCRIPTION

Reference is now made to the accompanying drawings, which illustrate various pertinent features of the technology disclosed herein.

As noted above, the present patent application relates to composite springs, composite spring assemblies, and the like, for use in medical devices, such as orthotic devices and prosthetic devices. The composite springs generally comprise alternating layers of a carbon fiber material and a fiberglass material.

Figure 1:
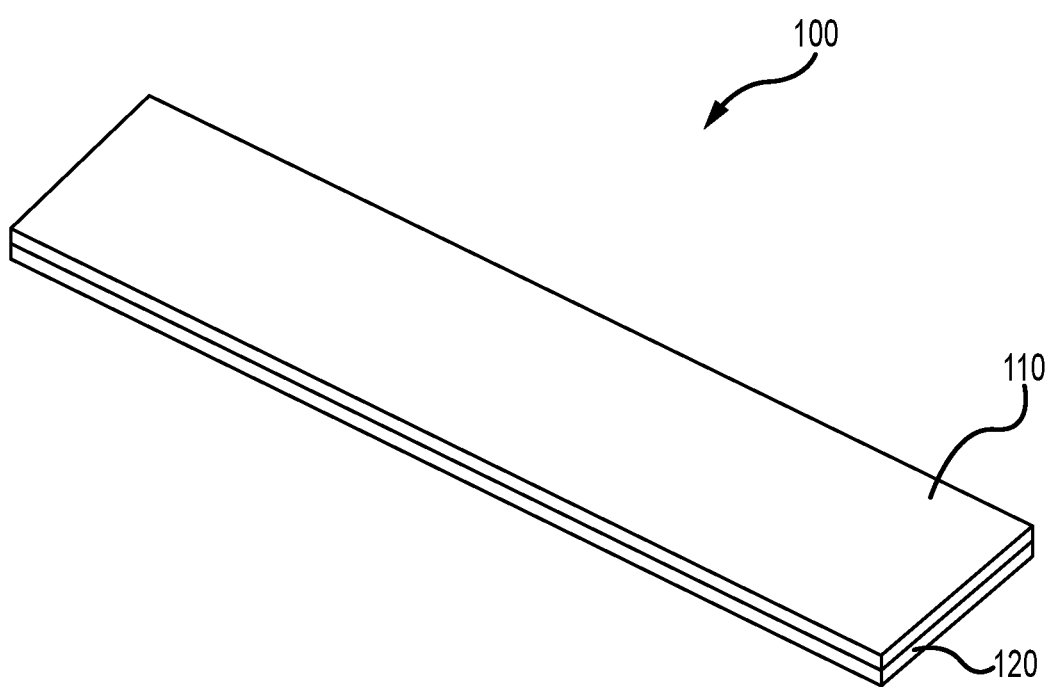
FIG. 1 is a schematic, perspective view of one embodiment of a composite spring (100).

Referring now to FIG. 1, one non-limiting embodiment of a composite spring (100) is shown. In the illustrated embodiment, the composite spring comprises a first layer (110) and a second layer (120). The first layer (110) generally comprises one of a carbon fiber material and a fiberglass material, and the second layer (120) generally comprises the other of a carbon fiber material and the fiberglass material. In one embodiment, the first layer (110) comprises a carbon fiber material and the second layer (120) comprises a fiberglass material. In another embodiment, the first layer (110) comprises a fiberglass material and the second layer (120) comprises a carbon fiber material. An adhesive (not illustrated) is generally used to bind the first layer (110) and the second layer (120) to one another. While the composite spring (100) of FIG. 1 is shown as having only two layers, multiple alternating layers may be used, as explained in further detail below.

As noted above, the composite spring (100) includes a carbon fiber material. As used herein, "carbon fiber material" means a material made from carbon fibers. Suitable carbon fibers include, for instance, twill, weave, unidirectional, or satin weave. The composite spring (100) may include a single type of carbon fiber material, or the composite spring may include multiple different types of carbon fiber materials. In one embodiment, the carbon fiber material comprises a carbon fiber fabric, such as 3 k 2×2 carbon fiber weave, manufactured by FIBRE GLAST. In one embodiment, a carbon fiber fabric has a thickness of from 0.10 to 1 mm. In one embodiment, a carbon fiber fabric is a carbon fiber weave. In one embodiment, the carbon fiber weave is a herring-bone weave-type.

As noted above, the composite spring (100) includes a fiberglass material. As used herein, "fiberglass material" means a material made from glass fibers. Suitable fiberglass materials include, for instance, E-glass or S-glass. The composite spring (100) may include a single type of fiberglass material, or the composite spring may include multiple different types of fiberglass materials. In one embodiment, the fiberglass material is a fiberglass fabric, such as the S2 fiberglass fabric made by FIBRE GLAST. In one embodiment, a fiberglass fabric has a thickness of 0.10 to 1 mm.

The first layer (110) may be any suitable shape adapted to facilitate providing a spring force to a composite spring assembly, as is described in further detail below. In the illustrated embodiment, the first layer (110) is in the shape of a rectangular strip. A strip geometry may facilitate, for instance, ease of manufacturing and/or an appropriate composite spring force and/or spring response.

In one approach, the first layer (110) comprises a thickness of from about 0.1 to about 1.0 mm. In one embodiment, the first layer (110) has a thickness of at least 0.15 mm. In another embodiment, the first layer has a thickness of at least 0.20 mm. In one embodiment, the first layer (110) has a thickness of not greater than 0.80 mm. In another embodiment, the first layer (110) has a thickness of not greater than 0.60 mm. In another embodiment, the first layer (110) has a thickness of not greater than 0.50 mm.

In one embodiment, the first layer (110) comprises a width of from to 3 mm to 12 mm. In one embodiment, the width of the first layer is at least 4 mm. In another embodiment, the width of the first layer is at least 5 mm. In another embodiment, the width of the first layer is at least 6 mm. In one embodiment, the width of the first layer is not greater than 10 mm. Other widths (smaller than 3 mm and greater than 12 mm) may be used.

In one embodiment, the first layer (110) comprises a length sufficient to facilitate provision of a non-linear spring force to a composite spring assembly. For instance, when used in a knee brace, the length of the first layer (110) may be from 50 to 250 mm. Shorter lengths may be used in smaller orthotic devices (e.g., in elbow, ankle, foot, and/or wrist braces) and/or prosthetic devices. Longer lengths may be used in larger orthotic devices and/or larger prosthetic devices.

In one approach, the length of the first layer (110) is from 50 to 250 mm. In one embodiment, the length of the first layer is at least 75 mm. In another embodiment, the length of the first layer is at least 100 mm. In yet another embodiment, the length of the first layer is at least 125 mm. In one embodiment, the length of the first layer is not greater than 225 mm. In another embodiment, the length of the first layer is not greater than 200 mm. In another embodiment, the length of the first layer is not greater than 175 mm.

In one embodiment, the length of the first layer (110) is at least 2 times the width of the first layer (110). In another embodiment, the length of the first layer (110) is at least 5 times the width of the first layer (110). In yet another embodiment, the length of the first layer (110) is at least 10 times the width of the first layer (110). In another embodiment, the length of the first layer (110) is at least 20 times the width of the first layer (110). In yet another embodiment, the length of the first layer (110) is at least 25 times the width of the first layer (110). The use of such length-to-width ratios may facilitate an appropriate spring force/response in a composite spring assembly.

The second layer (120) may be any suitable shape adapted to facilitate providing a spring force to a composite spring assembly, as is described in further detail below. In the illustrated embodiment, the second layer (120) is in the shape of a rectangular strip. In the illustrated embodiment, the first layer (110) and the second layer (120) have generally the same size. Thus, the second layer (120) may realize any of the thicknesses, widths, lengths and/or length-to-width ratios described above relative to the first layer (110). In other embodiments, the first layer (110) and the second layer (120) may be different shapes and/or sizes.

As noted above, an adhesive (not shown) may be used to bind the first layer (110) and the second layer (120) to one another. In one embodiment, the adhesive is a strength adhesive. In one embodiment, the strength adhesive is a thermosetting resin, such as an epoxy resin, a polyimide resin, an unsaturated polyester resin, or combinations thereof. In another embodiment, the strength adhesive is a thermoplastic resin, such as a polysulfonic resin, a polyethersulfonic resin, a polycarbonate resin, a polyetherketone resin, a polyetheretherketone resin, an aromatic polyamide resin, a polyetherimide resin, a thermoplastic polyimide resin, or combinations thereof. In one embodiment, the strength adhesive is an epoxy resin. For ease of reference, "epoxy resins" are sometimes referred to herein as "epoxy." In one embodiment, an epoxy is applied to the composite spring (100) by a resin injection process wherein an appropriate epoxy (e.g., a 2-part epoxy resin) is applied under vacuum to the layers (110, 120) of the composite spring (100). In one embodiment, a 2-part epoxy resin is used. In one approach, a ratio of the first part (A) of the epoxy resin to the second part (B) of the epoxy resin is from 2:1 to 7:1 (A:B). Such resin ratios may facilitate, for instance, an appropriate adhesive strength for binding layers of the composite spring (100). In one embodiment, the ratio of the first part (A) to the second part (B) is at least 2.5:1 (A:B). In another embodiment, the ratio of the first part (A) to the second part (B) is at least 3.0:1 (A:B). In another embodiment, the ratio of the first part (A) to the second part (B) is at least 3.25:1 (A:B). In one embodiment, the ratio of the first part (A) to the second part (B) is not greater than 6:1 (A:B). In another embodiment, the ratio of the first part (A) to the second part (B) is not greater than 5:1 (A:B). In another embodiment, the ratio of the first part (A) to the second part (B) is not greater than 4:1 (A:B).

Figure 2:
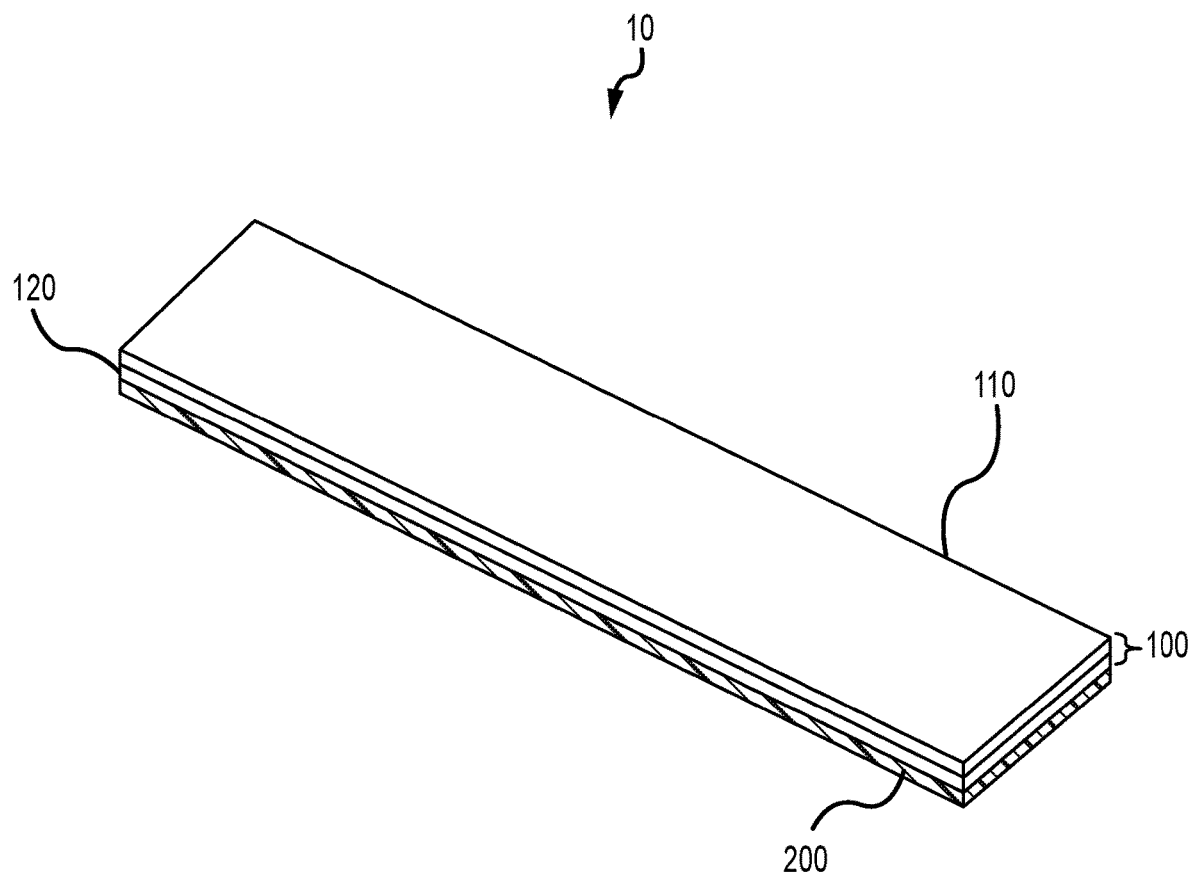
FIG. 2 is a schematic, perspective view of one embodiment of a composite spring assembly (10) having a composite spring (100) adhered to a dampening member (200) via an adhesive (300).
Figure 3:
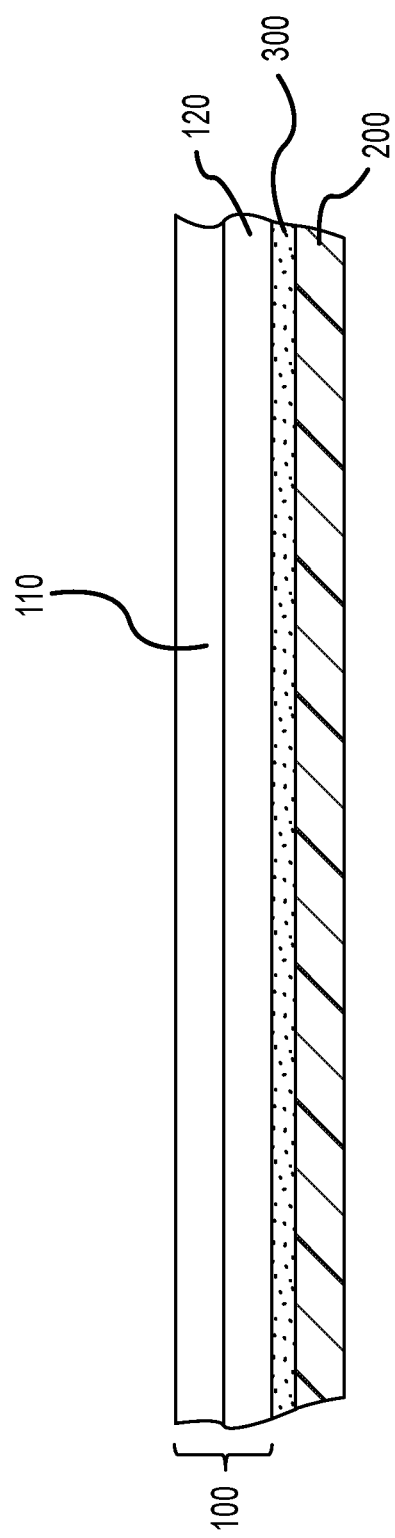
FIG. 3 is a cross-sectional, side-view of a portion of the composite spring assembly (10) of FIG. 2.

Referring now to FIGS. 2-3, one embodiment of a composite spring assembly (10) is illustrated. In the illustrated embodiment, the composite spring assembly (10) comprises a composite spring (100) having a first layer (110) and a second layer (120). The composite spring assembly also comprises a dampening member (200). An adhesive (300) generally binds the composite spring (100) and the dampening member (200) to one another.

The dampening member (200) facilitates dampening of the spring force of the composite spring (100). For instance, when the composite spring assembly (10) is sufficiently deflected (e.g., during movement an orthotic device, such as by movement of a joint), potential energy is stored. As this deflection force is removed, the potential energy may be released in the form of kinetic energy. The dampening member (200) facilitates dampening of the energy release, thereby providing a controlled release of energy from the composite spring assembly to the patient. Dampening may, for instance, restrict, minimize and/or prevent the user/wearer from incurring injury (e.g., joint damage) due to a spring member too rapidly applying a return spring force.

The dampening member (200) may be any suitable material for dampening the elastic force of a composite spring (200). In the illustrated embodiment, the dampening member (200) is shown as being a dampening plastic. As used herein, "dampening plastic" means a plastic material suited for dampening an elastic force. The composite spring assembly (10) may include a single type of a dampening plastic, or the composite spring may include multiple different types of dampening plastics. In one embodiment, a dampening plastic comprises a nylon material, i.e., a material comprising a synthetic linear polyamide or "PA." Suitable nylon-based plastic materials include nylon 6, nylon 6.6, and oilon, as well as the ONYX version of nylon available from MARKFORGED. Other types of engineered plastics such as acetal (polyoxymethylene), HDPE, PET, polypropylene, polypropylene, polyurethane, PTFE, PVC, and UHMWPE may also or alternatively be used to dampen elastic forces. In another embodiment, the dampening member (200) comprises a non-plastic material, such as a natural rubber and/or cellulose material, among others. In another embodiment, the dampening member itself is a laminate such as TUF-NOL.

The dampening member (200) may be any size and shape suited to dampen the composite spring (100). In the illustrated embodiment, the dampening member (200) is in the shape of a rectangular strip. In the illustrated embodiment, the first layer (110), the second layer (120) and the dampening member (200) have generally the same size and shape. Thus, the dampening member (200) may realize any of the thicknesses, widths, lengths and/or length-to-width ratios described above relative to the first layer (110) and the second layer (200). In other embodiments, the dampening member has a different size and/or shape relative to the first layer (110) and/or the second layer (120).

The thickness of the composite spring assembly (10) may be any thickness suitable for use in providing a non-linear spring response in an orthotic or prosthetic device. In one embodiment, the thickness is from 1.8 mm to 4.8 mm.

As noted above, an adhesive (300) may be used to bind the composite spring (100) and the dampening member (200) to one another. In the illustrated embodiment, the adhesive (300) is shown as being in the form of a layer disposed between the dampening member (200) and the composite spring (100). However, any suitable manner of binding the dampening member (200) and the composite spring (100) may be used.

The adhesive (300) may be any suitable adhesive adapted to bind the dampening member (200) and the composite spring (100). In one embodiment, the adhesive (300) is a dampening adhesive. For purposes of the present patent application, a dampening adhesive generally realizes a lower adhesive strength than a strength adhesive. Thus, a dampening adhesive may at least partially assist in dampening a spring force of a composite spring assembly. A dampening adhesive may be any adhesive suitable for dampening a spring force of a composite spring assembly. In one embodiment, a dampening adhesive comprises a cyanoacrylate adhesive.

Figure 4A:
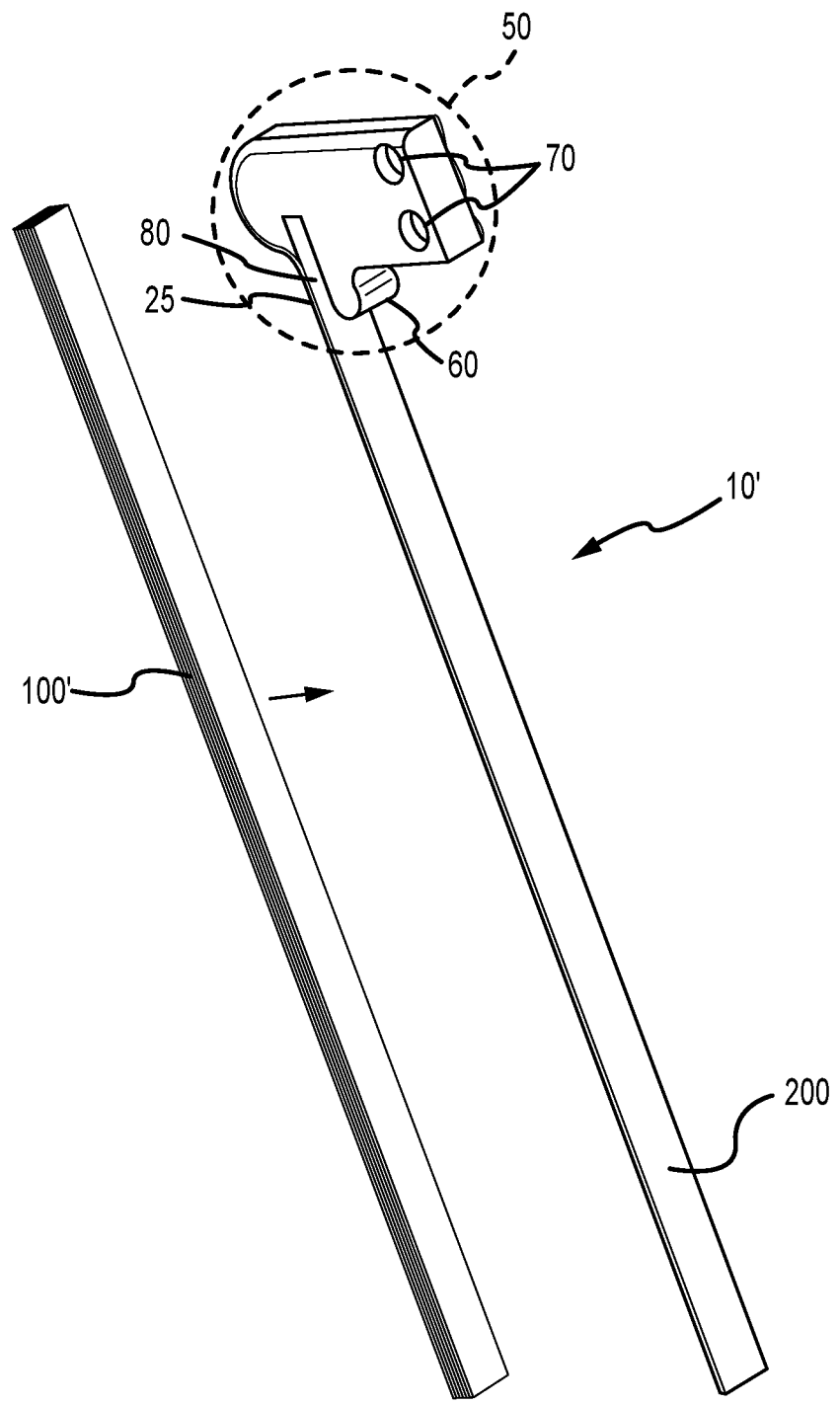
FIG. 4A is an exploded, perspective view of another embodiment of a composite spring assembly (10'), the composite spring assembly (10') comprising a composite spring (100) and a base (25), the base (25) comprising a dampening member (200), a head (50) and a fulcrum (60).
Figure 4B:
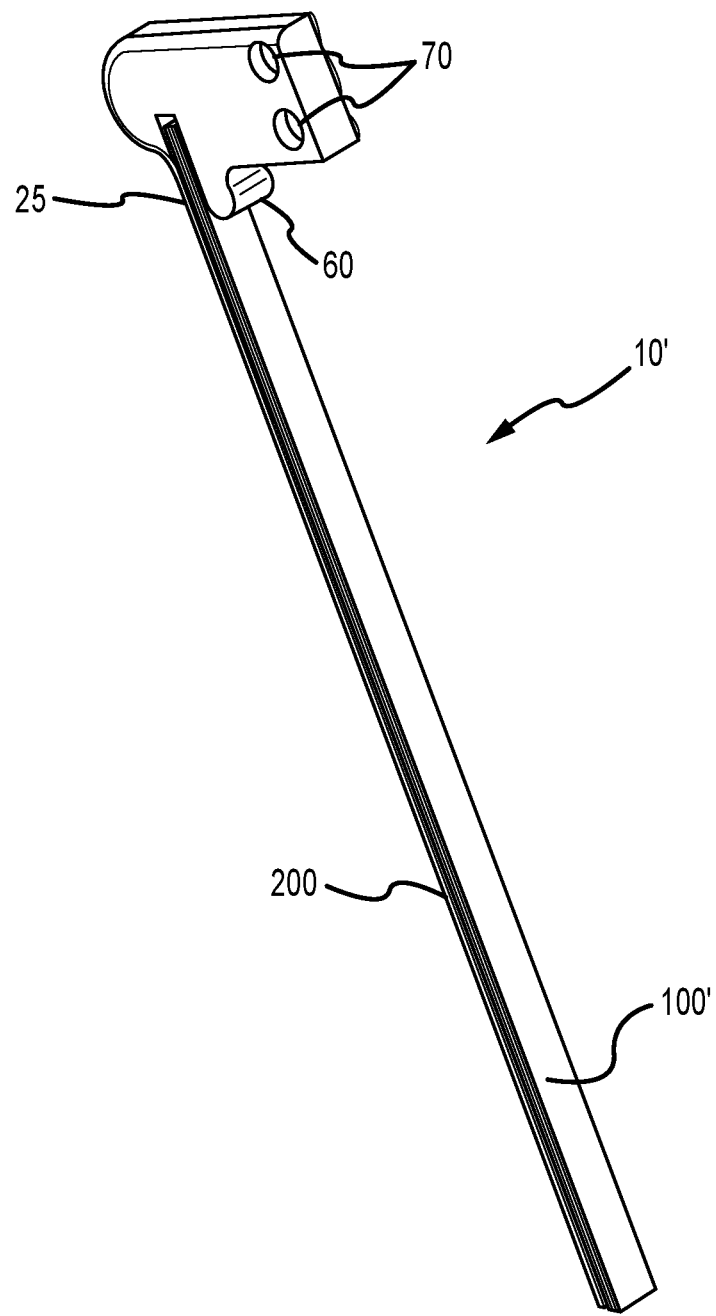
FIG. 4B is an assembled, perspective view of the composite spring assembly (10') of FIG. 4A.

Referring now to FIGS. 4A-4B, another embodiment of a composite spring assembly (10') is shown. In the illustrated embodiment, the composite spring assembly (10') comprises a composite spring (100') and a base (25). The base (25) comprises a dampening member (200). The base (25) further comprises a head (50). The head (50) comprises a fulcrum (60) and at least one aperture (70). A slot (80) is located between the fulcrum (60) and the dampening member (200). In one embodiment, the head (50) and the dampening member (200) of the base (25) are integral. In one embodiment, additive manufacturing is used to produce the base (25), thereby realizing the integral head (50) and dampening member (200). In another embodiment, the head (50) and dampening member (200) are separate components. In one embodiment (not illustrated), the head (50) is at least partially attached to the composite spring (100').

In one embodiment, the composite spring assembly (10') is assembled by applying an adhesive (not illustrated), such as a dampening adhesive, to surfaces of the dampening member (200) and/or the composite spring (100'). Subsequently, the composite spring (100') is placed proximal to and then bound to the dampening member (200) via the adhesive. As shown in FIG. 4B, the composite spring (100') may be placed above and in-line with the dampening member (200) such that lateral sides of both items are aligned. In the illustrated embodiment, a carbon fiber material of the composite spring (100') is adhered to the dampening member (200). In other embodiments, the fiberglass material of the composite spring (100') may be adhered to the dampening member (200).

As illustrated in FIG. 4B, the slot (80) may facilitate proper placement of the composite spring (100') relative to the dampening member (200) and/or the fulcrum (60). As illustrated in FIG. 4B, only a portion of the composite spring (100') is located within the slot (80). In combination with fulcrum (60), proper placement of the composite spring (100') within slot (80) may facilitate a proper moment arm for the composite spring assembly (10'). In one embodiment, not greater than 50% of the volume of the composite spring (100') is located within the slot. In another embodiment, not greater than 40% of the volume of the composite spring (100') is located within the slot. In yet another embodiment, not greater than 30% of the volume of the composite spring (100') is located within the slot. In another embodiment, not greater than 20% of the volume of the composite spring (100') is located within the slot. In yet another embodiment, not greater than 10% of the volume of the composite spring (100') is located within the slot. As illustrated in FIG. 4B, a small gap (not numbered) may exist between the distal end of the composite spring (100') and a distal end of the slot (80). In other embodiments, the distal end of the composite spring (100') is located fully within the slot (80).

Figure 4C:
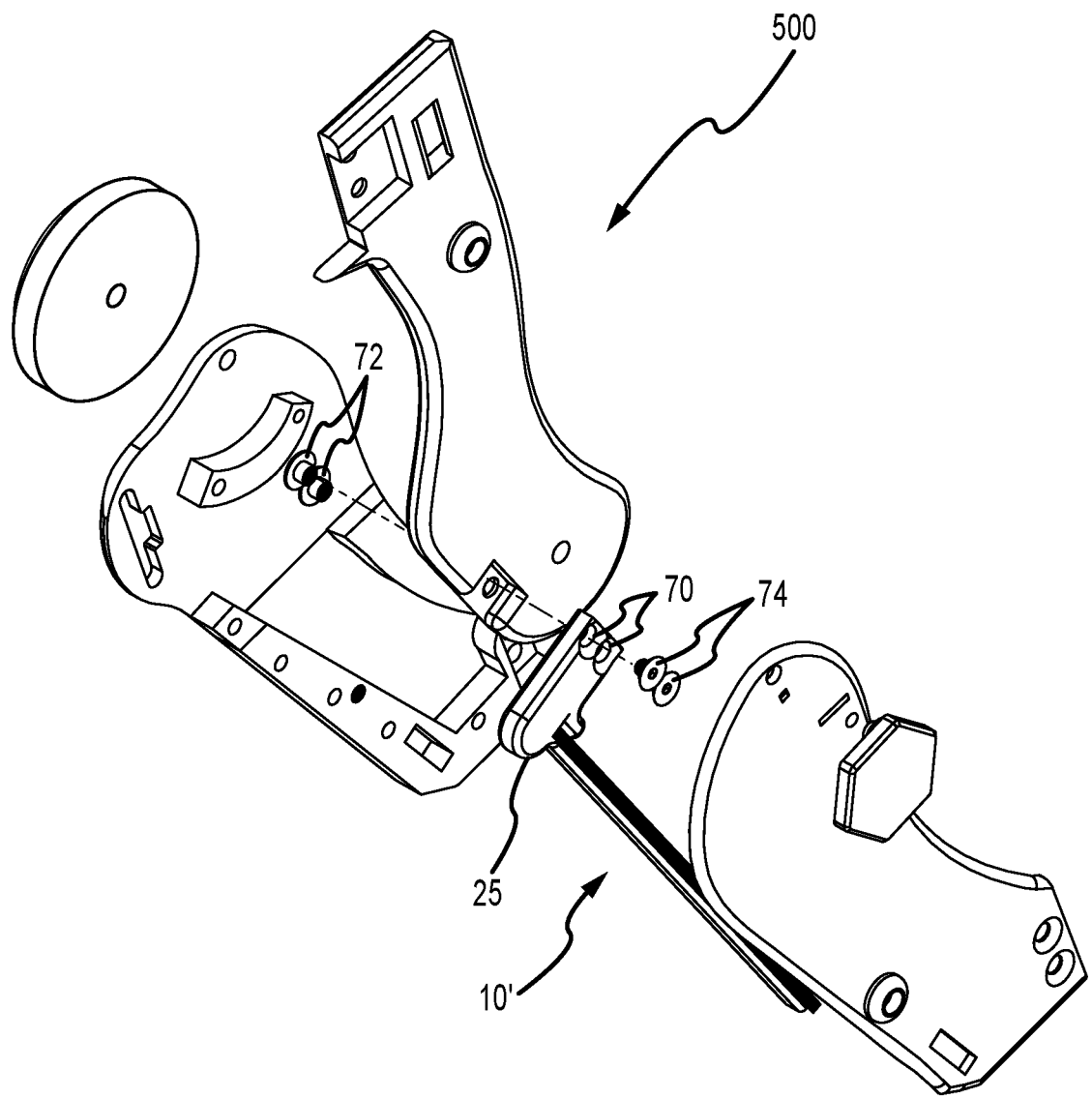
FIG. 4C is an exploded view of a knee brace (500) incorporating the composite spring assembly (10') of FIG. 4B.
Figure 4D:
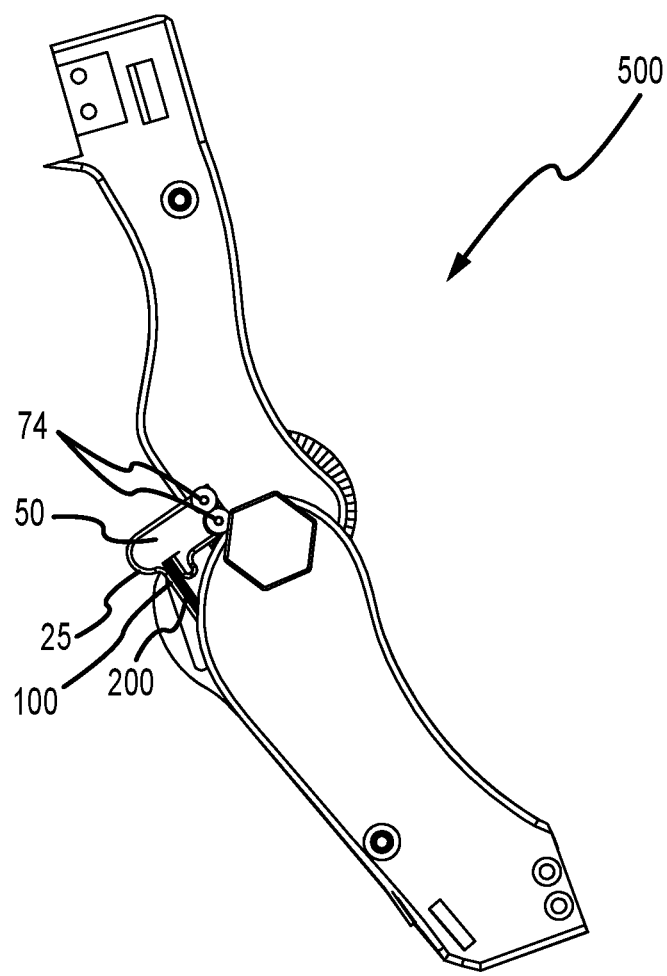
FIG. 4D is side, assembled view of the knee brace of FIG. 4C.

The head (50) may facilitate attachment of the composite spring assembly (10') to a medical device. For instance, and referring now to FIGS. 4C-4D, the one or more apertures (70) of the head (50) may align with one or more corresponding protrusions or apertures (72) of an orthotic device (500), which in the illustrated embodiment is in the form of a knee brace. Thus, the head (50) and its corresponding apertures (70) facilitate repeated and reliable attachment of a composite spring assembly (10') to a corresponding orthotic device (500). In one embodiment, a fastener (74), such as a screw, is used to attach the composite spring assembly (10') to the corresponding orthotic device (500) via the one or more apertures (70). In another embodiment, a snap-fit arrangement is used, wherein the orthotic device (500) comprises one or more protrusions (not illustrated) adapted to snap-fit with the one or more apertures (70) of the composite spring assembly (10'). Accordingly, a distal end of the composite spring assembly (10') is fixed relative to the orthotic device (500). The proximal end of the composite spring assembly (10') is generally unattached and moves freely about a moment arm. Thus, the composite spring assembly (10') is cantilevered during operation of the orthotic device (500) and delivers a non-linear spring response. In one embodiment, the orthotic device is a knee brace, such as any of the knee braces described in commonly-owned U.S. Patent Application Publication No. 2019/0209358, which knee brace disclosures are incorporated herein by reference in their entirety. Similar arrangements may be used with prosthetic devices.

As shown in FIGS. 4A-4D, the head (50) may comprise one or more apertures (70) to facilitate attachment of the composite spring assembly (10') to the orthotic device (500). In other embodiments (not illustrated), the head (50) may also or alternatively comprise one or more protrusions for engaging with an orthotic device. Thus, the head (50) may comprise one or more apertures, one or more protrusions, or any combination of aperture(s) and protrusion(s) to facilitate attachment of the composite spring assembly (10') to the orthotic device (500). Similar arrangements may be used with prosthetic devices.

In the illustrated embodiment of FIGS. 4A-4B, the composite spring (100') comprises six alternating layers of carbon fiber (C) and fiberglass (F), i.e., a C-F-C-F-C-F layering. This arrangement is illustrated in FIG. 5A, with three carbon layers (120a, 120b, and 120c) and three fiberglass layers (110a, 110b, and 110c). For some devices, such as some adult-sized knee braces, it has been found that a six-layer composite spring (100') structure provides an appropriate non-linear spring force/response for a joint.

Figure 5B:
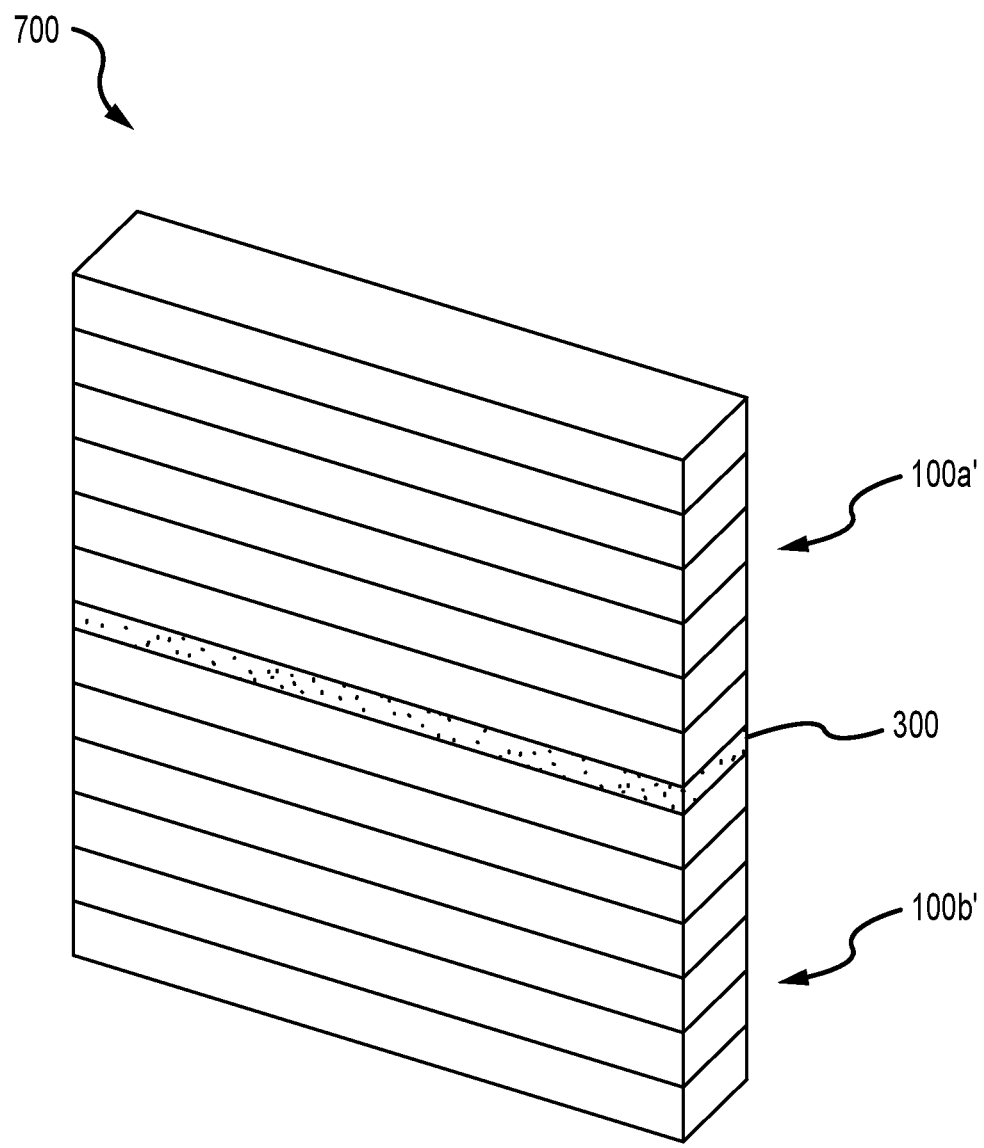
FIG. 5B is a perspective view of one embodiment of a multi-component composite spring (700).

In some embodiments, and referring now to FIG. 5B, a multi-component composite spring (700) may be employed, wherein two or more composite springs (100') are utilized. As used herein, a multi-component composite spring is a spring having multiple composite springs. Any suitable number of composite springs may be used in a multi-component composite spring system. In the illustrated embodiment of FIG. 5B, the multi-component composite spring (700) comprises a first composite spring (100a') and a second composite spring (100b'). An adhesive (300) is used to bind the first composite spring (100a') and the second composite spring (100b') to one another. In the illustrated embodiment, the adhesive (300) is shown as being in the form of a layer disposed between the first composite spring (100a') and the second composite spring (100b'). However, any suitable manner of binding the first composite spring (100a') and the second composite spring (100b') may be used. In one embodiment, the adhesive (300) is a dampening adhesive. Use of a dampening adhesive may facilitate dampening of elastic forces of the multi-component composite spring (700). For instance, use of more than six layers in a composite spring may result in inappropriate forces being applied and/or an inappropriate spring response. The use of a dampening adhesive located between composite springs may facilitate appropriate spring forces and with appropriate dampening effects. As may be appreciated, the multi-component composite spring (700) of FIG. 5B may be employed with the base (25) of FIGS. 4A-4B in lieu of the single component composite spring (100') illustrated therein.

The composite springs and/or composite spring assemblies described herein may be tailored based on application. For instance, the six-layer structure of FIG. 5A may be appropriate for many knee brace applications. However, in some instances, less layers may be appropriate (e.g., for pediatric applications). Similarly, for elbow brace applications, the six-layer structure of FIG. 5A may also be suitable, but in some instances fewer layers may be used, while in some instances more layers may be used. Similar principles apply to other orthotic devices, such as ankle, foot, and/or wrist braces. Similar principles also apply to prosthetic devices employing the composite springs described herein.

Further, multi-component springs may be used in orthotic devices and/or prosthetic devices, and such multi-component springs may be tailored based on end-use application. Even further, while the figures generally show composite springs having an even number of layers, any number of carbon fiber layers and fiberglass layers may be used. Thus, a composite spring may comprise any number of layers, whether that be an odd number (3, 5, 7, etc.) or an even number (2, 4, 6, etc.) of layers. Even further, while alternating layers of carbon fiber and fiberglass materials have been described, in some instances, adjacent layers of the same material may be used. For instance, in some embodiments a first carbon fiber layer may be adjacent to and directly connected to a second carbon fiber layer (e.g., for a C-C-F configuration). Similarly, in some embodiments, a first fiberglass layer may be adjacent to and directly connected to a second fiberglass layer (e.g., for a F-F-C configuration).

Figure 6:
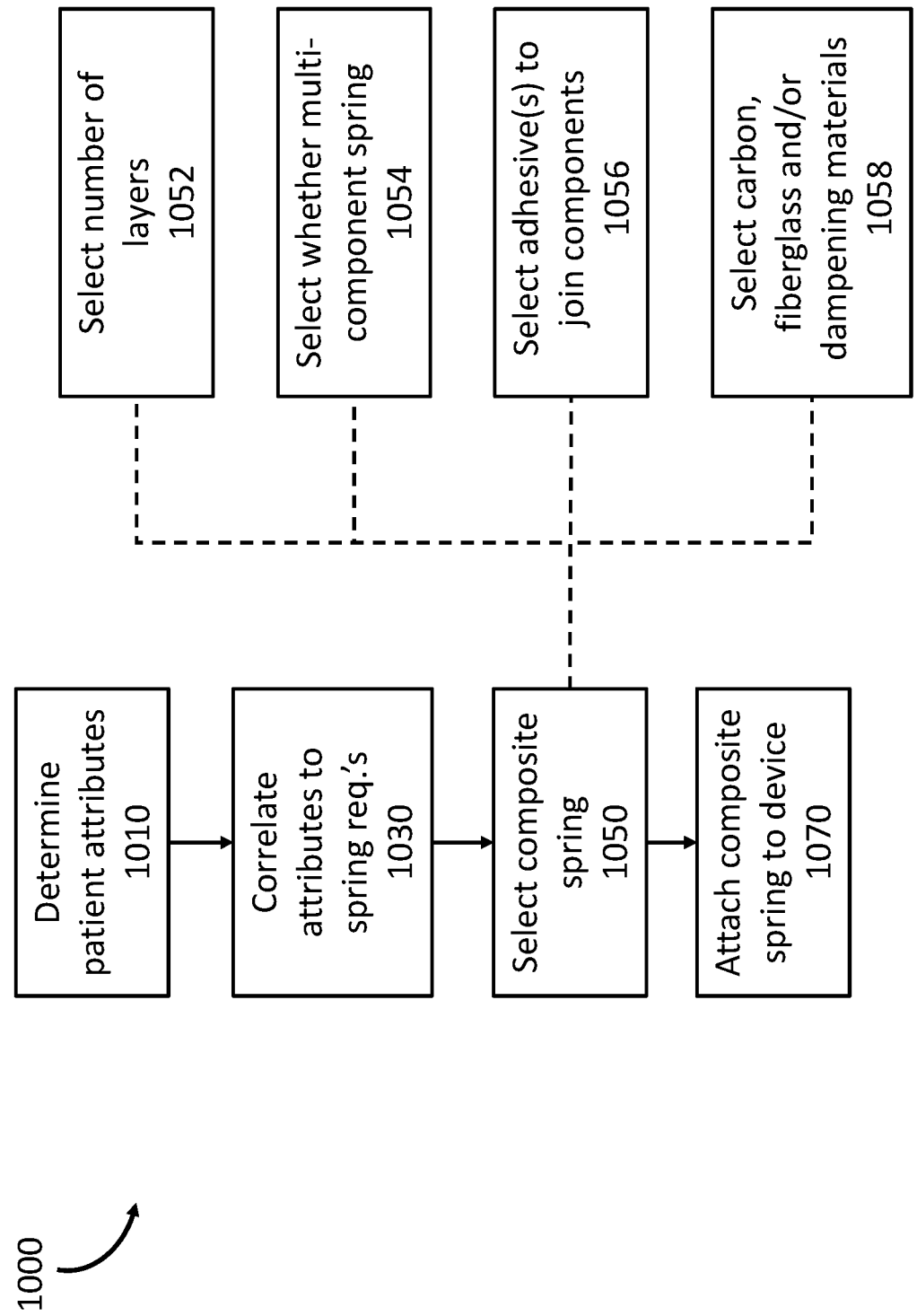
FIG. 6 is a flow chart showing one embodiment of a method of for producing medical devices comprising a composite spring based on patient attributes.

The composite springs and/or composite spring assemblies described herein may be tailored based on patient attributes. For instance, a larger individual may require a different composite spring arrangement than a smaller individual. In one embodiment, and referring now to FIG. 6, in one embodiment, a method (1000) comprises determining (1010) patient attributes of a patient who will use/receive an orthotic device and/or prosthetic device having one or more composite springs therein. The patient attributes may be one or more of gender, height, weight, body type, age, and muscle density, among others.

The method (1000) may further comprise correlating (1030) one or more of the patient attributes to appropriate composite spring characteristics. Some non-limiting examples of composite spring characteristics include flexibility, strength and rigidity, among others.

The method (1000) may further include selecting (1050) an appropriate composite spring and/or composite spring assembly based on one or more of the determining step (1010) and the correlating step (1030). For instance, one or more of the following may be selected:
  the number of composite spring layers (1052);
  whether to employ a multi-component spring (1054);
  which adhesive(s) to use (1056);
  which materials to use for the carbon fiber, fiberglass and dampening member materials (1058).

In one embodiment, the selecting step (1050) comprises selecting a pre-built composite spring and/or a composite spring assembly. For instance, in some circumstances, a pre-built composite spring assembly, such as that shown in FIGS. 4A-4B may be suitable for a patient's orthotic device and/or prosthetic device. In another embodiment, the selecting step comprises selecting a custom composite spring and/or composite spring assembly. For instance, with larger patients requiring a larger knee brace, the correlating step (1030) may indicate that a multi-component spring may be required due to the additional forces imparted due to the load of the larger patient. As another example, with smaller patients requiring an elbow brace, a composite spring having only four alternating layers of carbon fiber and fiberglass (i.e., C-F-C-F) may be appropriate. After the appropriate composite spring and/or composite spring assembly is selected (1050), it may be attached (1070) to the medical device (e.g., an orthotic device; a prosthetic device).

In one embodiment, a computerized database is used wherein one or more patient attributes of a patient are inputted into a computer. The computer may correlate those patient attribute(s) to the requisite composite spring characteristics, optionally taking into account the end use application for the device. The computer may utilize the composite spring characteristics to complete the selecting step, thereby selecting one or more of (a) the number of composite spring layers to use (1052), (b) whether to employ a multi-component spring (1054), (c) the adhesive(s) to employ (1056), and (d) which materials to use for the carbon fiber, fiberglass and dampening member materials (1038). The computer may then output the recommended configuration, after which the appropriate composite spring and/or composite spring assembly selected (and custom built, if needed) and then attached to the orthotic device and/or prosthetic device (1070). Accordingly, customized orthotic devices and/or prosthetic devices may be readily and quickly configured and produced, and in a manner that was not heretofore possible.

The figures constitute a part of this specification and include illustrative embodiments of the present disclosure and illustrate various objects and features thereof. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references, unless the context clearly dictates otherwise. The meaning of "in" includes "in" and "on", unless the context clearly dictates otherwise.

While various embodiments of the new technology described herein have been described in detail, it is apparent that modifications and adaptations of those embodiments will occur to those skilled in the art. However, it is to be expressly understood that such modifications and adaptations are within the spirit and scope of the presently disclosed technology.

What is claimed is:

1. A composite spring assembly comprising:
   (a) a composite spring having a first component and a second component;
      wherein the first component comprises alternating layers of a carbon fabric and a fiberglass fabric;
      wherein the second component comprises alternating layers of the carbon fiber fabric and the fiberglass fabric;
      wherein, for both the first component and the second component, a strength adhesive adheres the carbon fiber fabric to the fiberglass fabric;
      an adhesive joining the first component to the second component;
   (b) a dampening member attached to the composite spring;
   (c) a head attached to at least the dampening member, wherein the head is adapted to attach to a medical device, wherein the medical device is an orthotic device, wherein the orthotic device is a knee brace, wherein during movement of the orthotic device, the composite spring provides a non-linear spring response.

2. The composite spring assembly of claim 1, wherein the head comprises a slot.

3. The composite spring assembly of claim 2, wherein portions of the first component and the second component are located in the slot.

4. The composite spring assembly of claim 3, wherein not greater than 50% of the volume of the first component is located in the slot.

5. The composite spring assembly of claim 4, wherein the head comprises a fulcrum, wherein, when the first component is sufficiently deflected, the fulcrum is configured to engage an upper portion of the first component.

6. A method comprising:
   determining at least one patient attribute for an orthotic patient;
   correlating the at least one patient attribute to at least one composite spring requirement for the orthotic patient;
   based on the determining step, selecting a composite spring for use in an orthotic device for the orthotic patient; and
   attaching the selected composite spring to the orthotic device.

7. The method of claim 6, wherein the selecting step comprises selecting a number of alternating layers of carbon fiber and fiberglass for the composite spring.

8. The method of claim 7, wherein the alternating layers comprise at least three carbon fiber layers and at least three fiberglass layers.

9. The method of claim 7, comprising:
   based on the determining step, selecting a multi-component composite spring for use in the orthotic device;
   wherein the alternating layers define a first component of the composite spring assembly;
   wherein the composite spring assembly comprises a second component attached to the first component, wherein the second component comprises alternating layers of carbon fiber and fiberglass.

10. The method of claim 9, wherein a dampening adhesive joins the first component to the second component.

11. The method of claim 10, wherein, for both the first component and the second component, a strength adhesive binds the alternating layers of the carbon fiber and the fiberglass.

12. A composite spring assembly comprising:
   (a) a composite spring having a first component and a second component;
      wherein the first component comprises alternating layers of a carbon fabric and a fiberglass fabric;

wherein the second component comprises alternating layers of the carbon fiber fabric and the fiberglass fabric;

wherein, for both the first component and the second component, a strength adhesive adheres the carbon fiber fabric to the fiberglass fabric;

an adhesive joining the first component to the second component;

(b) a dampening member attached to the composite spring;

(c) a head attached to at least the dampening member, wherein the head is adapted to attach to a medical device, wherein the head comprises a slot.

13. The composite spring assembly of claim 12, wherein portions of the first component and the second component are located in the slot.

14. The composite spring assembly of claim 13, wherein not greater than 50% of the volume of the first component is located in the slot.

15. The composite spring assembly of claim 12, wherein the head comprises a fulcrum, wherein, when the first component is sufficiently deflected, the fulcrum is configured to engage an upper portion of the first component.

16. The composite spring assembly of claim 1, wherein the dampening member is attached to the composite spring by a dampening adhesive having a lower adhesion strength than the strength adhesive.

17. The composite spring assembly of claim 1, wherein the strength adhesive comprises a thermosetting resin or a thermoplastic resin.

18. The composite spring assembly of claim 1, wherein the composite spring assembly has a thickness of from 1.8 mm to 4.8 mm.

19. The method of claim 6, wherein the at least one patient attribute comprises at least one of gender, height, weight, body type, age, and muscle density.

20. The method of claim 11, wherein the strength adhesive comprises an epoxy and the dampening adhesive comprises a cyanoacrylate adhesive.

* * * * *